(12) United States Patent
Miasnikov et al.

(10) Patent No.: US 9,759,667 B2
(45) Date of Patent: Sep. 12, 2017

(54) MINIATURE AIR GAP INSPECTION CRAWLER

(71) Applicant: General Electric Company, Schenectady, NY (US)

(72) Inventors: Nicholas Aleksander Miasnikov, Glenville, NY (US); Jason Royal Gammans, Rotterdam, NY (US); Richard Michael Hatley, Convent Station, NJ (US); Sean Michael McDonnell, Berkeley Heights, NJ (US); Antonio Ernesto Giannattasio, Whippany, NJ (US)

(73) Assignee: General Electric Company, Schenectady, NY (US)

( * ) Notice: Subject to any disclaimer, the term of this patent is extended or adjusted under 35 U.S.C. 154(b) by 253 days.

(21) Appl. No.: 14/534,405

(22) Filed: Nov. 6, 2014

(65) Prior Publication Data
US 2016/0131595 A1    May 12, 2016

(51) Int. Cl.
*G01R 31/34* (2006.01)
*G01D 21/00* (2006.01)
*G01N 21/94* (2006.01)
*G02B 23/24* (2006.01)
*H04N 5/225* (2006.01)

(52) U.S. Cl.
CPC ......... *G01N 21/94* (2013.01); *G02B 23/2476* (2013.01); *H04N 2005/2255* (2013.01)

(58) Field of Classification Search
CPC .. G01N 21/94; G02B 23/2476; H04N 5/2251; H04N 2005/2255
See application file for complete search history.

(56) References Cited

U.S. PATENT DOCUMENTS

| | | | | |
|---|---|---|---|---|
| 4,794,912 | A * | 1/1989 | Lia | G02B 23/2476 600/152 |
| 4,803,563 | A * | 2/1989 | Dailey | G01R 31/34 324/220 |
| 4,934,786 | A * | 6/1990 | Krauter | G02B 23/2476 385/118 |
| 5,668,421 | A * | 9/1997 | Gladish | B60L 13/10 104/23.2 |
| 6,225,813 | B1 * | 5/2001 | Garwatoski | G01R 27/2617 324/551 |
| 7,201,055 | B1 * | 4/2007 | Bagley | H02K 15/00 376/249 |

(Continued)

*Primary Examiner* — Tat Chio
*Assistant Examiner* — Patrick Demosky
(74) *Attorney, Agent, or Firm* — James W. Pemrick; Ernest G. Cusick; Frank A. Landgraff

(57) ABSTRACT

A system for inspecting a dynamoelectric machine is provided. The dynamoelectric machine includes a rotor, a stator and a radial gap existing between the rotor and the stator. The system includes a sled configured for insertion into the radial gap between the rotor and the stator. The sled is configured to transport an optical device along the radial gap. The optical device obtains an image of the radial gap, a portion of the rotor and a portion of the stator. The sled is configured for attachment to a push rod and the push rod is used to move the sled and optical device along the radial gap. The system is configured for entry into a single end of the dynamoelectric machine.

17 Claims, 9 Drawing Sheets

(56) References Cited

U.S. PATENT DOCUMENTS

| | | | |
|---|---|---|---|
| 7,343,828 B2* | 3/2008 | Bagley | G01R 31/34 73/865.8 |
| 7,555,966 B2 | 7/2009 | Bagley et al. | |
| 7,681,452 B2* | 3/2010 | Bagley | G01H 9/008 73/618 |
| 8,220,345 B2* | 7/2012 | Moser | G01R 31/34 73/866.5 |
| 8,275,558 B2 | 9/2012 | Reed et al. | |
| 8,370,086 B2 | 2/2013 | Reed | |
| 8,378,691 B2 | 2/2013 | Moser et al. | |
| 9,345,462 B2* | 5/2016 | Weitzner | A61B 1/0014 |
| 2007/0277629 A1* | 12/2007 | Bagley | B62D 63/02 73/865.8 |
| 2008/0097292 A1* | 4/2008 | Cabiri | A61B 1/00082 604/95.01 |
| 2008/0275299 A1* | 11/2008 | Park | A61B 1/00156 600/115 |
| 2009/0087080 A1 | 4/2009 | Ahn et al. | |
| 2009/0146680 A1* | 6/2009 | Moser | H02K 15/00 324/765.01 |
| 2013/0135457 A1 | 5/2013 | Kell et al. | |

\* cited by examiner

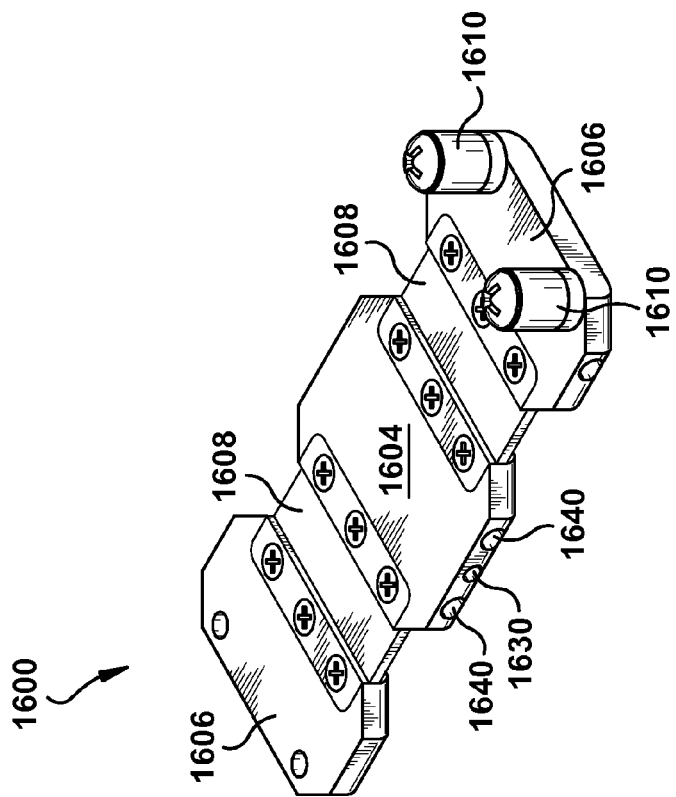
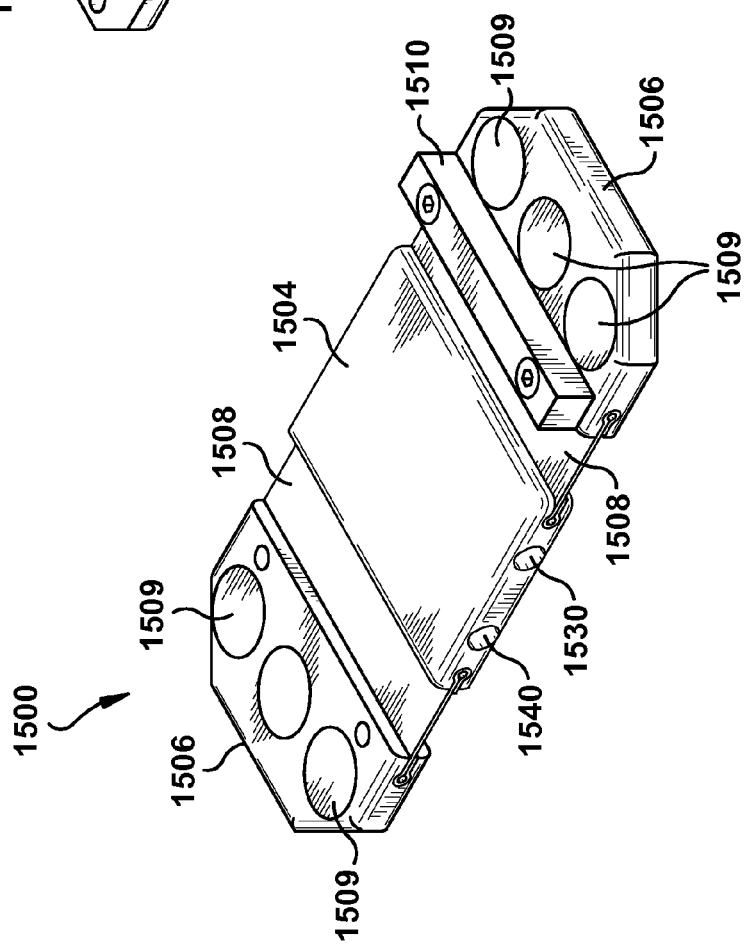

MINIATURE AIR GAP INSPECTION CRAWLER

BACKGROUND OF THE INVENTION

The invention relates generally to the assessment of the condition of dynamoelectric machines. More particularly, the invention relates to a system and method for inspecting dynamoelectric machines, particularly electric generators.

Dynamoelectric machines such as electric generators include a rotor and a stator. Rotors are generally constructed from a steel forging and include a number of slots that run the length of the rotor. Rotors are electrically wound by placing conductors referred to as rotor windings into the slots of the rotor. Stators are generally constructed from a number of stacked, metal laminations. Stators also include slots, which run the length of the stator. Stators are electrically wound by placing conductors known as stator coils into the armature slots of the stator.

Conventional stator coils are frequently held in place in stator slots using a retention assembly such as a stator wedge assembly including a stator wedge, a top retaining ripple spring, and one or more shims. In this configuration, a stator coil is placed into an armature slot, a shim is placed above the stator coil, a top ripple spring is placed above the shim, and a stator wedge having a beveled edge is driven into a groove near the head of the armature slot, securing the stator coil, the shim, and the top ripple spring. The top ripple spring provides compressive force to keep the stator coils held firmly in the armature slot.

Over time and during use of the dynamoelectric machine, stator wedges may become loose. If a stator wedge becomes loose, it can permit a stator coil to vibrate, which can cause catastrophic failure in an electric generator. In order to avoid such vibration, it is desirable to periodically inspect the tightness of the wedge assembly. Such inspections present a challenge, because the wedge assembly is difficult to access within a generator.

BRIEF DESCRIPTION OF THE INVENTION

According to a first aspect of the invention, a system is provided for inspecting a dynamoelectric machine. The dynamoelectric machine includes a rotor, a stator and a radial gap existing between the rotor and the stator. The system includes a sled configured for insertion into the radial gap between the rotor and the stator. The sled is configured to transport an optical device along the radial gap. The optical device is configured to obtain an image of at least one of the radial gap, a portion of the rotor and a portion of the stator. The sled is configured for attachment to a push rod and the push rod is used to move the sled and optical device along the radial gap. The system is configured for entry into a single end of the dynamoelectric machine.

According to another aspect of the invention, a system is provided for inspecting a dynamoelectric machine. The dynamoelectric machine includes a rotor, a stator and a radial gap existing between the rotor and the stator. The system includes a first sled configured for insertion into the radial gap between the rotor and the stator. The first sled is configured to transport an optical device along the radial gap. The optical device is configured to obtain an image of at least one of the radial gap, a portion of the rotor and a portion of the stator. The first sled is configured for attachment to a push rod and the push rod is used to move the first sled and optical device along the radial gap. A second sled has an aperture, and an elongated guide member is configured to cooperate with transportation of the second sled. An expandable bladder is located at one end of the elongated guide member, and the elongated guide member includes a conduit configured to supply a gas to the bladder for inflation and deflation of the bladder. The elongated guide member is configured to pass through the aperture so that the second sled travels back and forth along the elongated guide member. The system is configured for entry into a single end of the dynamoelectric machine.

According to a still further aspect of the invention, a method for inspecting or servicing a dynamoelectric machine, includes the steps of placing a sled in a radial gap between a rotor and a stator of the dynamoelectric machine. The sled is configured for insertion into the radial gap, and to transport an optical device along the radial gap. The optical device is configured to obtain an image of the radial gap. The sled is configured for attachment to a push rod and the push rod is used to move the sled and optical device along the radial gap. A navigating step is used for navigating the sled axially along the radial gap by pushing or pulling on the push rod. An inspecting step is used for inspecting the radial gap by viewing an image produced from the optical device to identify the presence of any foreign object or debris. A retrieving step is used for retrieving and removing any foreign object or debris identified in the inspecting step. The placing step may also include installing an elongated guide member between the stator and the rotor and securing at least one end of the elongated guide member by inflating a bladder. The bladder is configured to wedge itself between the rotor and stator once inflated. The placing step may also include placing the sled over the elongated guide member, and installing at least one of the optical device and a retrieval device through one or more ports in the sled.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

FIG. 15 is a perspective view of a sled, according to an aspect of the present invention.

FIG. 16 is a perspective view of a sled, according to an aspect of the present invention.

DETAILED DESCRIPTION OF THE INVENTION

At least one embodiment of the present invention is described below in reference to its application in connection with the operation of a dynamoelectric machine. Although embodiments of the invention are illustrated relative to a dynamoelectric machine in the form of a generator, it is understood that the teachings are equally applicable to other electric machines including, but not limited to motors. Further, at least one embodiment of the present invention is described below in reference to a nominal size and including a set of nominal dimensions. However, it should be apparent to those skilled in the art that embodiments of the present invention are likewise applicable to any suitable generator and/or engine. Further, it should be apparent to those skilled in the art that embodiments of the present invention are likewise applicable to various scales of the nominal size and/or nominal dimensions.

Figures 1, 2:
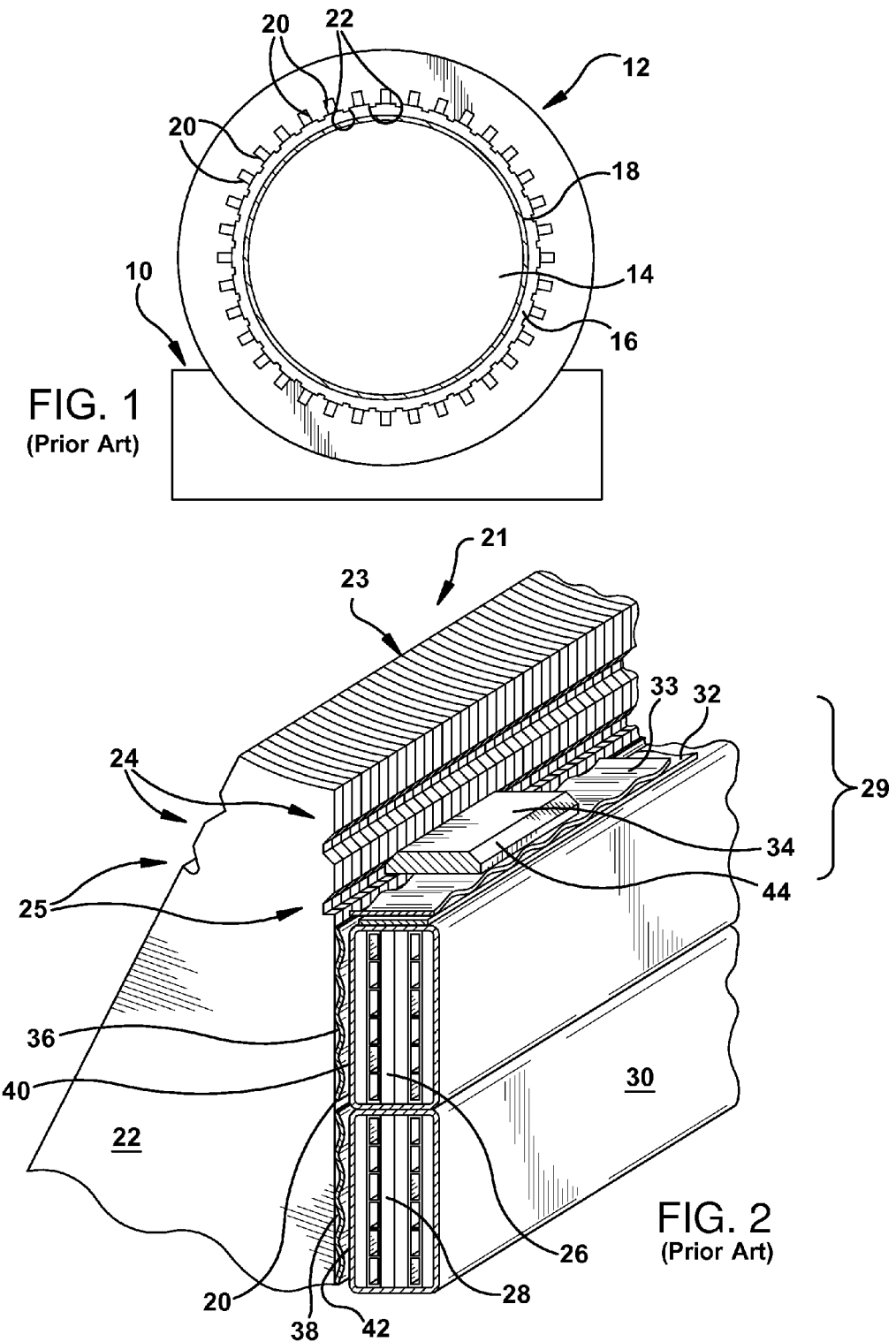
FIG. 1 shows a diagrammatic cross sectional view of a conventional electric generator having a rotor installed within a stator.
FIG. 2 shows a partial isometric view of a conventional stator in an electric generator as depicted in FIG. 1.

FIG. 1 shows a cross sectional view of a conventional electric generator or dynamoelectric machine 10, including a stator 12 surrounding a rotor 14. A narrow radial gap 16 exists between the stator 12 and retaining ring 18 or rotor 14. The retaining ring 18 can be disposed about a portion of rotor 14. In some generators, radial gap 16 may be as narrow as about 3.8 cm (about 1.5 inch), although it may be either wider or narrower in various embodiments. Stator 12 includes an annular array of axially extending armature slots 20, each of which may be formed in stator 12 with a stator tooth 22 formed on either side thereof.

As shown in FIG. 2, each stator tooth 22 can be made of a plurality of punchings or laminations 23, and may include a pair of axially extending grooves 24, 25 which are radially disposed with respect to each other. Thus, each armature slot 20 typically includes two pairs of generally parallel grooves 24, 25 formed therein. Stator coils 26, 28, which may be partially or wholly wrapped in an insulation layer 30, are disposed in each of the armature slots 20 of stator 12. In a typical stator 12, a pair of stator coils 26, 28 is stacked within each armature slot 20, one radially disposed on top of the other. However, in other embodiments the stator tooth may have only one groove.

Stator coils 26, 28 are retained in armature slots 20 by wedge assembly 29. In some embodiments, wedge assembly 29 may be in the form of a stator wedge assembly, although any other type of wedge assembly may be used to retain coils 26, 28 in armature slots 20. As shown in FIG. 2, wedge assembly 29 may include a filler member, such as shim 32; a retaining ripple spring 33; and a wedging member or wedge 34. One or more shims 32 are typically placed radially inwardly from the top stator coil 26. Retaining ripple spring 33 may be disposed within the armature slot 20 radially inwardly from shim 32. Retaining ripple spring 33 may be made of, for example, glass fiber roving fabric bonded with a high temperature resistant synthetic resin matrix.

As further shown in FIG. 2, a filler member such as a first side ripple spring 36 may be disposed in armature slot 20, perpendicular to retaining ripple spring 33, between top stator coil 26 and stator tooth 22. Another filler member such a second side ripple spring 38 may be disposed in armature slot 20 perpendicular to retaining ripple spring 33 between bottom stator coil 28 and stator tooth 22. Optionally, one or more additional filler members such as first and second side slot fillers or shims 40, 42 may be placed between the side ripple springs 36, 38 and the respective stator coils 26, 28. Alternatively, side shims 40, 42 may be placed in armature slot 20 between stator tooth 22 and stator coils 26, 28 without side ripple springs 36, 38. Side ripple springs 36, 38 and side shims 40, 42 are designed to fill any axial gap that is created between stator coils 26, 28 and stator tooth 22 and to increase tightness between stator coils 26, 28 and stator tooth 22 in the tangential direction.

One or more wedges 34 may be installed within armature slot 20 radially inwardly from retaining ripple spring 33. Wedge 34 typically has beveled edges 44 which engage correspondingly shaped grooves 24, 25 in the side walls of stator tooth 22. Wedge 34 is installed by sliding the wedge 34 into at least one of parallel grooves 24, 25. Wedge 34 compresses retaining ripple spring 33 against shim 32, which is in turn compressed against top stator coil 26 to tightly secure stator coils 26, 28 radially within armature slot 20. In another embodiment, retaining ripple spring 33 may be located between wedge 34 and insulated stator coil 26 without shim 32 present.

Over time, retaining ripple spring 33 can lose resiliency such that the wedge 34 can become loose, permitting coils 26, 28 to vibrate. Such vibration of coils 26, 28 can result in damage to coils 26, 28 and failure of coil insulation 30. In addition, liberated or foreign material may become trapped in the radial gap 16. Inspection of wedge assembly 29 and radial gap 16 are therefore desirable to identify a need for corrective action before this occurs. For example, if foreign material is identified it can be removed before causing substantive damage.

Figure 3:
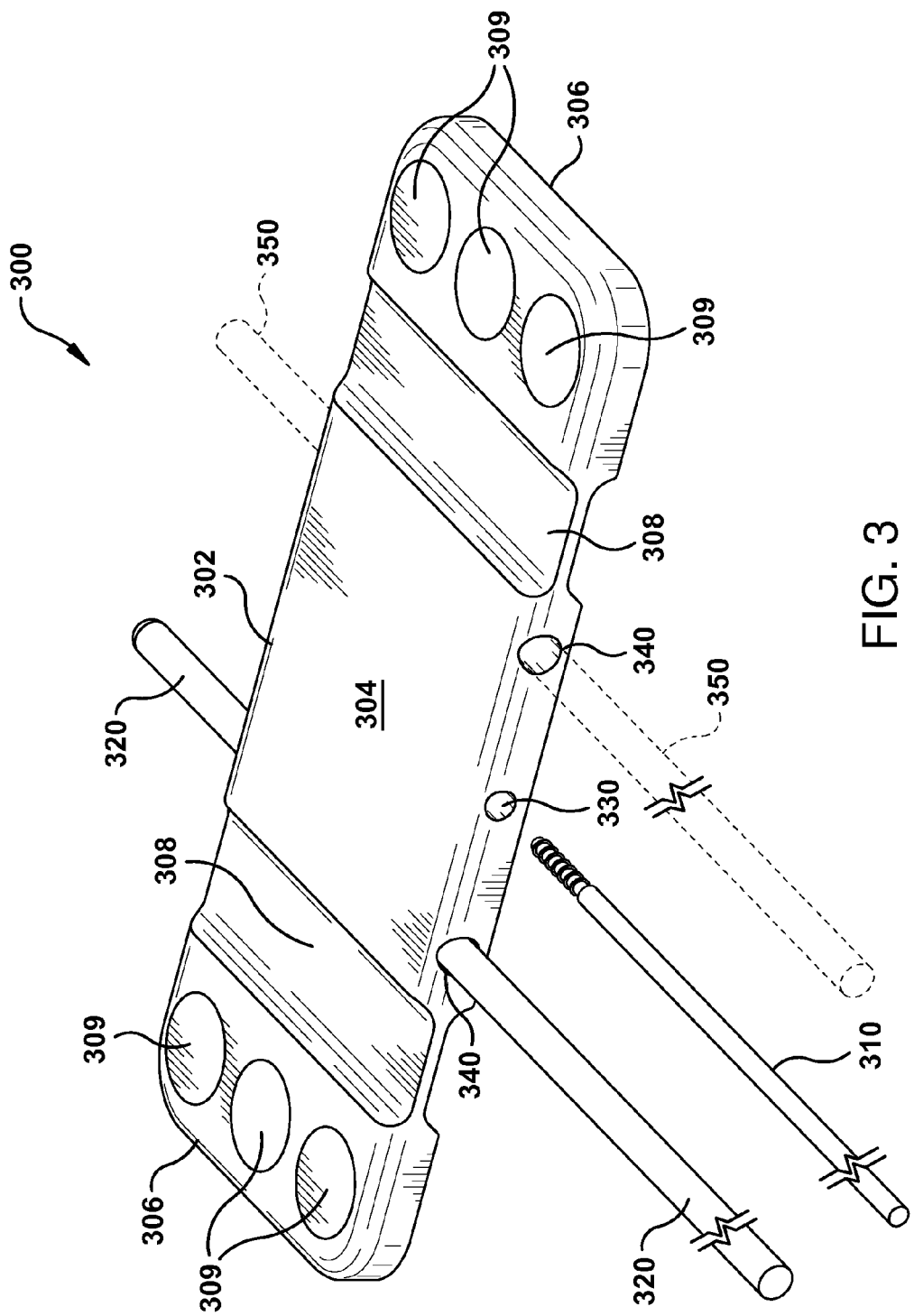
FIG. 3 illustrates a perspective view of a sled, according to an aspect of the present invention.

FIG. 3 illustrates a perspective view of a sled 300, according to an aspect of the present invention. The sled 300 is part of a system for inspecting a dynamoelectric machine, such as a motor or generator. The sled 300 is configured for insertion into the radial gap 16 that exists between the rotor 14 and stator 12, and is configured to transport an optical device 320 along the radial gap. The optical device 320 may be a borescope, camera or other suitable imaging or scanning device, which is configured to obtain an image of the radial gap 16 and a portion of the rotor 14 and a portion of the stator 12. The sled 300 is configured for attachment to a push rod 310 that is used to move the sled 300 and the optical device 320 along the radial gap 16. The push rod may be comprised of a substantially non-magnetic material and may have multiple sections configured to be connected to each other. The system is configured for entry into a single end of the dynamoelectric machine. This facilitates inspection as only one end of the machine will need to be opened up to allow insertion of the sled 300.

The sled 300 includes a main body 302 having a middle section 304, and two end sections 306. Each end section 306 is connected to the middle section 304 by a flexible member 308. The middle section 304, end sections 306 and flexible member 308 may be comprised of non-magnetic materials such as plastic, rubber, or non-magnetic metals or alloys. For example, if the main body 302 is formed of plastic, then the flexible members 308 could be formed of thinner portions of plastic, or corrugated plastic members. The flexible members 308 permit the end sections 306 to curve with the curved surface of the stator (or rotor). Magnets 309 are located in each of the end sections 306, and the magnets 309 may be flush with, protrude from or recessed with respect to the surface of the end section. For example, the magnets 309 could be located below a surface of the end section 306 to facilitate travel (by reducing friction) along a radially inner surface of the stator core. Multiple magnets 309 are shown, but it is to be understood that one magnet or more than one magnet could be used in each of the end sections 306.

The sled 300 includes an attachment point 330 for the push rod 310. The attachment point may be an internally threaded hole configured for use with external threads on the end of push rod 310. Alternatively, the push rod 310 may insert into a smooth hole 330 with a friction fit. One or more ports 340 are configured for operation with the optical device 320 or a retrieval device 350. The ports 340 pass through the middle section 304 and are configured and sized to permit the optical device 320 and the retrieval device 350 to slide back and forth through the ports 340.

Figure 4:
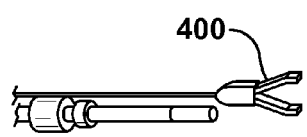
FIGS. 4-10 illustrate perspective views of various retrieval devices, according to aspects of the present invention.
Figure 5:
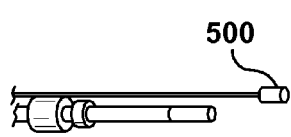
Figure 6:
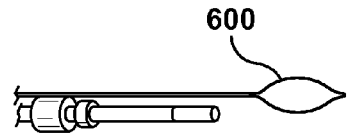
Figure 7:
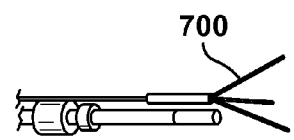
Figure 8:
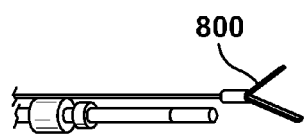
Figure 9:
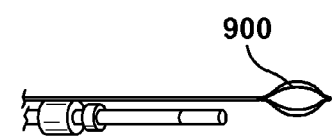
Figure 10:
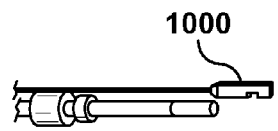

FIGS. 4-10 illustrate perspective views of various retrieval devices 350, according to aspects of the present invention. FIG. 4 illustrates an alligator clamp 400, which may be used to clamp down on items and to retrieve objects of various shapes. Any undesired foreign object or debris (FOD) should be removed from the radial gap to prevent damage to the dynamoelectric machine. FIG. 5 illustrates a magnet 500, which may be used to remove foreign objects or debris by magnetic force. The magnet 500 can reach inside tight spaces to remove metal and other magnetic objects. FIG. 6 illustrates a snare 600 that can snare FOD for retrieval and/or removal. FIG. 7 illustrates a multi-prong gripper 700 that can clasp onto FOD for retrieval and/or removal. FIG. 8 illustrates a fork and tine 800 that can securely grip onto FOD for retrieval and/or removal. FIG. 9 illustrates a multi-wire basket 900 that allows entrapment of FOD for retrieval and/or removal. FIG. 10 illustrates a wire cutter 1000 that may be used for cutting wire to aid in FOD retrieval and/or removal, or other machine servicing. All of the previously described retrieval devices may either be mounted in tandem with each other and passing through the same port 340, or the optical device 320 may pass through one port 340 and the retrieval device 350 may pass through a different port 340.

Figure 11:
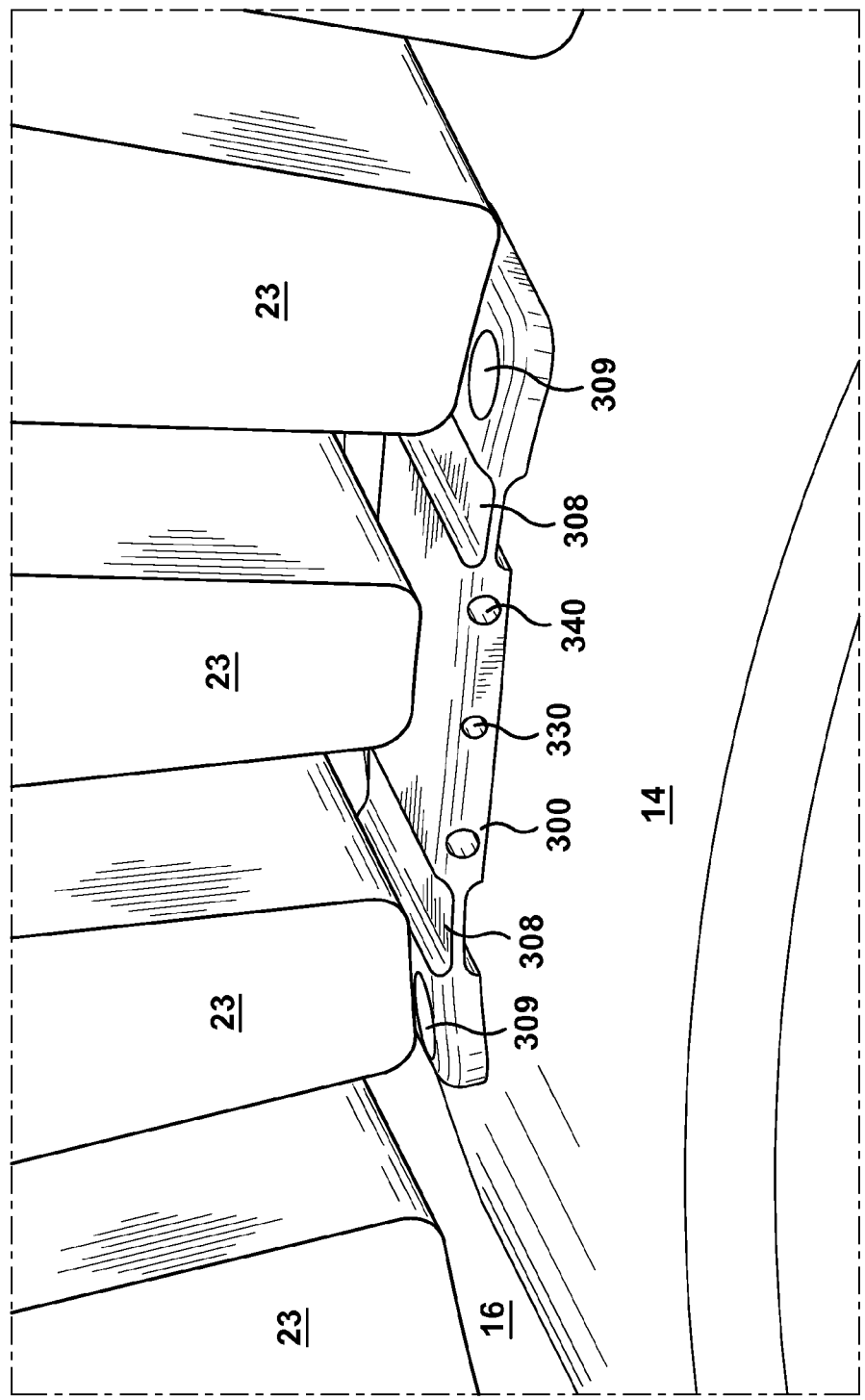
FIG. 11 illustrates a perspective view of the sled positioned in the radial gap, according to an aspect of the present invention.

FIG. 11 illustrates a perspective view of the sled 300 positioned in the radial gap 16, according to an aspect of the present invention. The push rod 310, optical device 320 and retrieval device 350 are omitted for clarity. As examples only, the radial gap 16 may be about 0.2 inches to about 0.4 inches in the radial direction. Accordingly, the thickness of the sled 300 is sized to be less than the dimension of the radial gap 16. The magnets 309 may be used to hold the sled to the stator core 23. In use, the sled 300 can be attached to the stator core 23, and then slid axially along the stator. The flexible members 308 allow the sled to conform to the arc of the inner portion of stator 12. As the sled 300 is either pushed into or pulled out of the stator by the push rod 310, the optical device 320 and/or retrieval device 350 can be used to inspect and repair the dynamoelectric machine. An advantage is that the sled can be inserted from a single end of the machine, thereby reducing machine disassembly and downtime. For example, the optical device can be used to detect foreign objects or material and the retrieval device can be used to remove the FOD.

Figure 12:
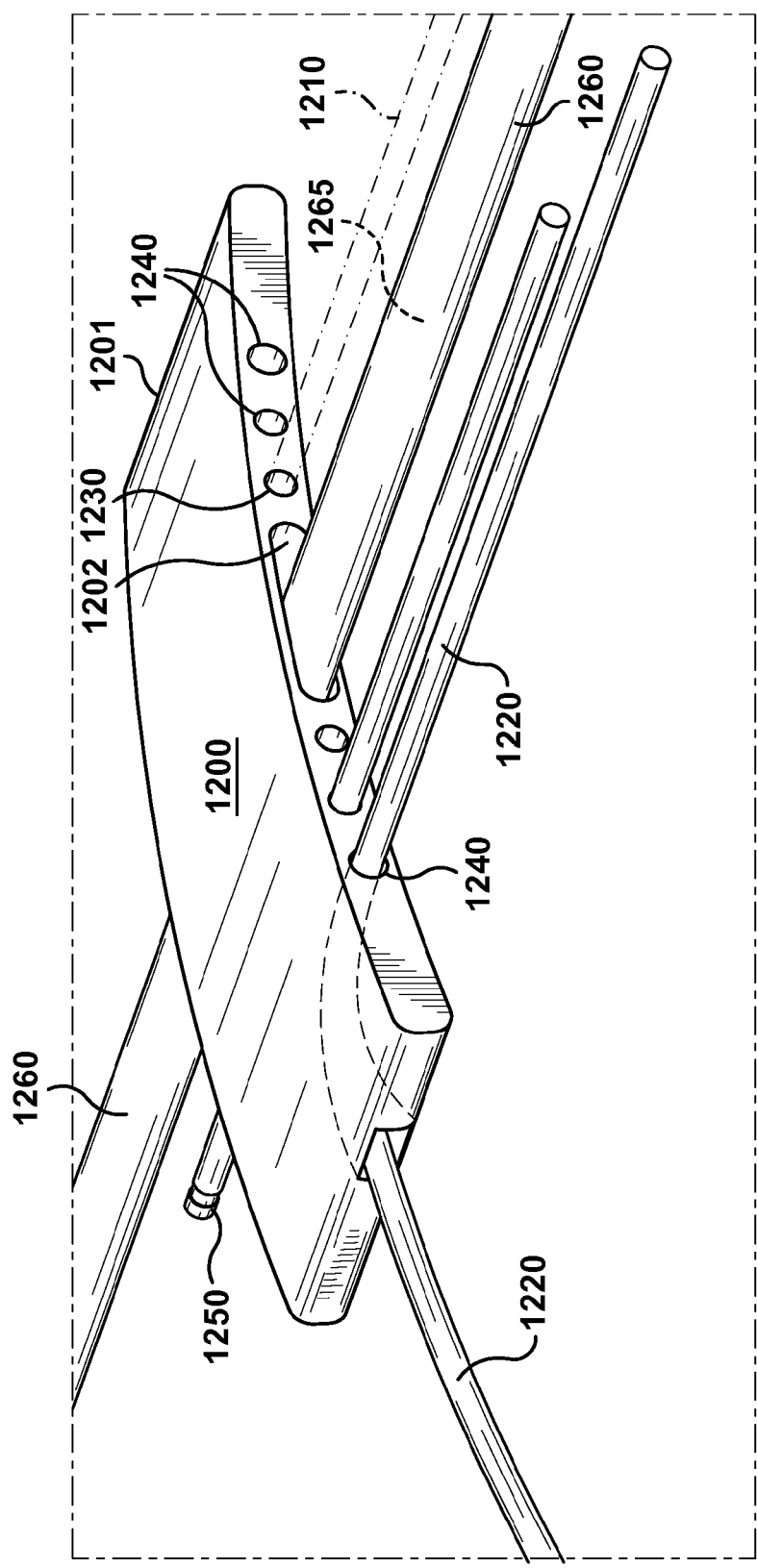
FIG. 12 illustrates a perspective view of a sled, according to an aspect of the present invention.

FIG. 12 illustrates a perspective view of a sled 1200, according to an aspect of the present invention. The sled 1200 has a main body 1201 that may be slightly curved to conform to the radially inner portion of stator 12. The main body also includes an attachment point 1230 for the push rod 310 and one or more ports 1240 configured for operation with an optical device 1220 or a retrieval device 1250. The ports 1240 are sized to permit the optical device 1240 and retrieval device 1250 to slide back and forth through the ports 1240. For example, the inner diameter of the ports 1240 are sized to be slightly larger than the outer diameter of the optical device's 1250 shaft/cable and the retrieval device's 1250 shaft/cable. The optical device 1220 may be a borescope, camera or other suitable imaging or scanning device, which is configured to obtain an image of the radial gap 16 and a portion of the rotor 14 and a portion of the stator 12. The retrieval device 1250 may be at least one of an alligator clamp, a magnet (as shown), a snare, a multi-prong gripper a fork and tine, a basket or a cutting tool (e.g., as illustrated in FIGS. 4-10). The sled 1200 is configured for attachment to a push rod 1210 that is used to manually move the sled 1200 and the optical device 1220 axially along the radial gap 16. The system is configured for entry into a single end of the dynamoelectric machine, and this facilitates inspection and service as only one end of the machine will need to be opened up to allow insertion of the sled 1200.

An elongated guide member 1260 is configured to cooperate with transportation of the sled 1200. The elongated guide member may include an expandable bladder 1370 located at one end of the elongated guide member 1260, and the elongated guide member 1260 includes a conduit configured to supply a gas to the bladder 1370 for inflation and deflation of the bladder 1370. The conduit 1265 may be located internal or external to the elongated guide member. For example, if the elongated guide member is comprised of a hollow webbing material, then the central (or hollow) portion of the webbing would form the conduit used to inflate and deflate the bladder 1370. The sled 1200 has an aperture 1202, and the elongated guide member 1260 is configured to pass through the aperture 1202 so that the sled travels back and forth along the elongated guide member 1260. The elongated guide member 1260 may be viewed as a zip-line in that the sled 1200 can slide back and forth along this "zip-line" (or elongated guide member 1260).

Figure 13:
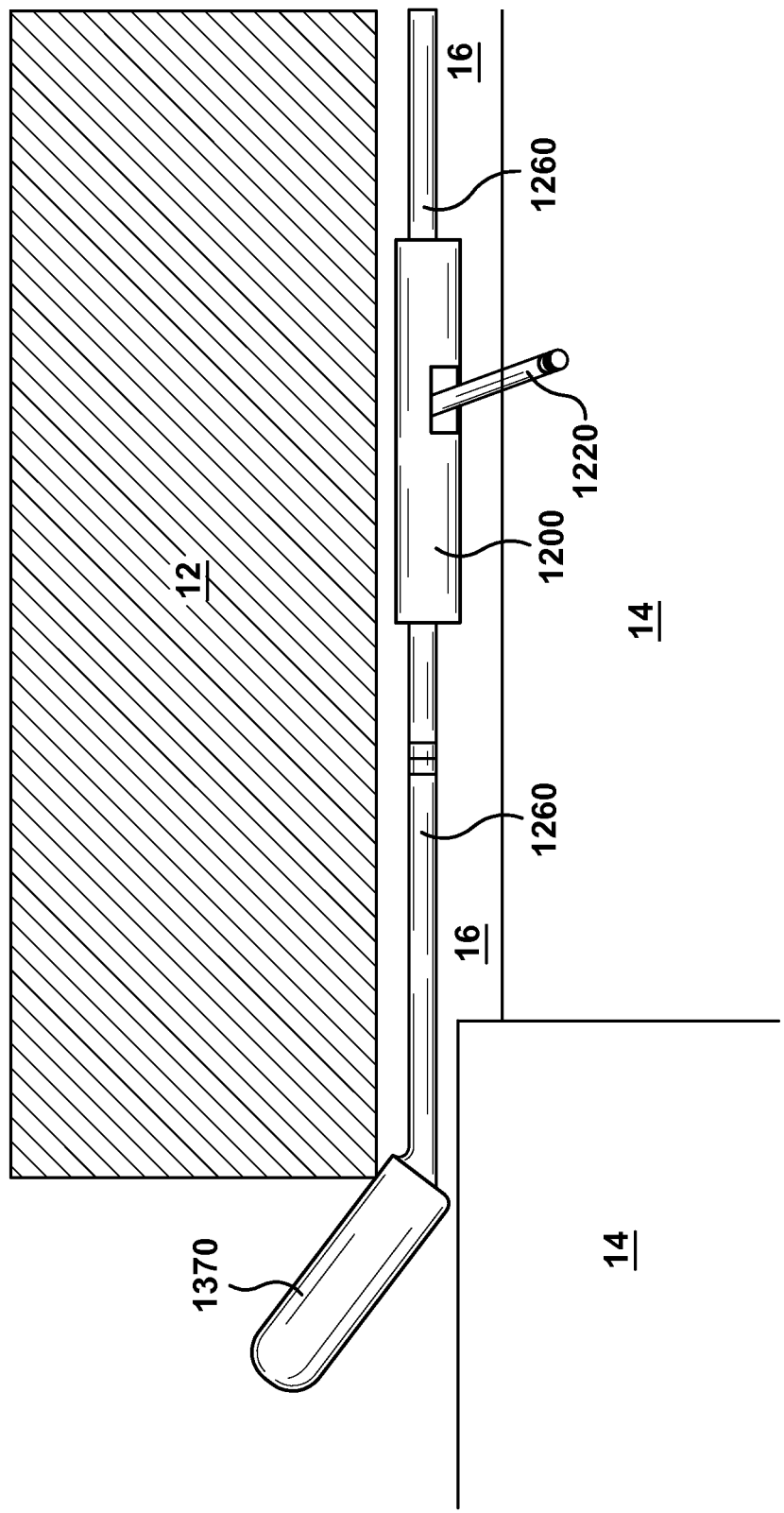
FIG. 13 illustrates a side view of the sled shown in FIG. 12 positioned in the radial gap of the dynamoelectric machine, according to an aspect of the present invention.

FIG. 13 illustrates a side view of the sled 1200 positioned in the radial gap 16, according to an aspect of the present invention. The elongated guide member 1260 has been placed in the radial gap 16 and the bladder 1370 is inflated to secure one end of the elongated guide member 1260. As the bladder 1370 inflates it wedges between the stator 12 and rotor 14, resulting in a secure mount to one end of the elongated guide member 1260. The other end of the elongated guide member 1260 may include another bladder 1370, or it may be tied off on a secure mounting location (such as the end windings). The push rod 1210 is used to manually slide the sled 1200 axially back and forth along the radial gap, and the optical device 1220 is used to view at least one of portions of the stator 12, portions of the rotor 14 and the radial gap 16. The optical device is flexible so that it can be pushed through sled 1200 and view regions near the sled 1200 or portions located away from the sled 1200. For example, if the sled 1200 (and elongated guide member 1260) is located at the top of the radial gap 16, then by retracting or keeping the imaging portion of the optical device near the sled 1200 the top portion of the radial gap could be viewed. The sled 1200 includes one or more ports 1240 that are configured to turn at an angle, for example, about 30 degrees to about 90 degrees. This allows the optical device 1220 to be pushed into and to extend down along the radial gap 16. In the example above, if the sled is located at the top of the radial gap, then the optical device's cable can be pushed into the sled so that the imaging portion of the optical device travels circumferentially around the radial gap and downward at the same time. In this manner, one entire side (i.e., 180 degrees) of the radial gap 16 can be inspected by extending and retracting the cable of the optical device. It is to be understood that multiple optical devices and/or retrieval devices could be used simultaneously with the sled 1200 to view, inspect and service both sides of the radial gap. Multiple elongated guide members, along with sleds 1200, could also be used to speed up the inspection and servicing process. For example, three elongated guide members, each with its own sled, could be arranged 120 degrees apart along the radial gap for rapid inspection.

Figure 14:
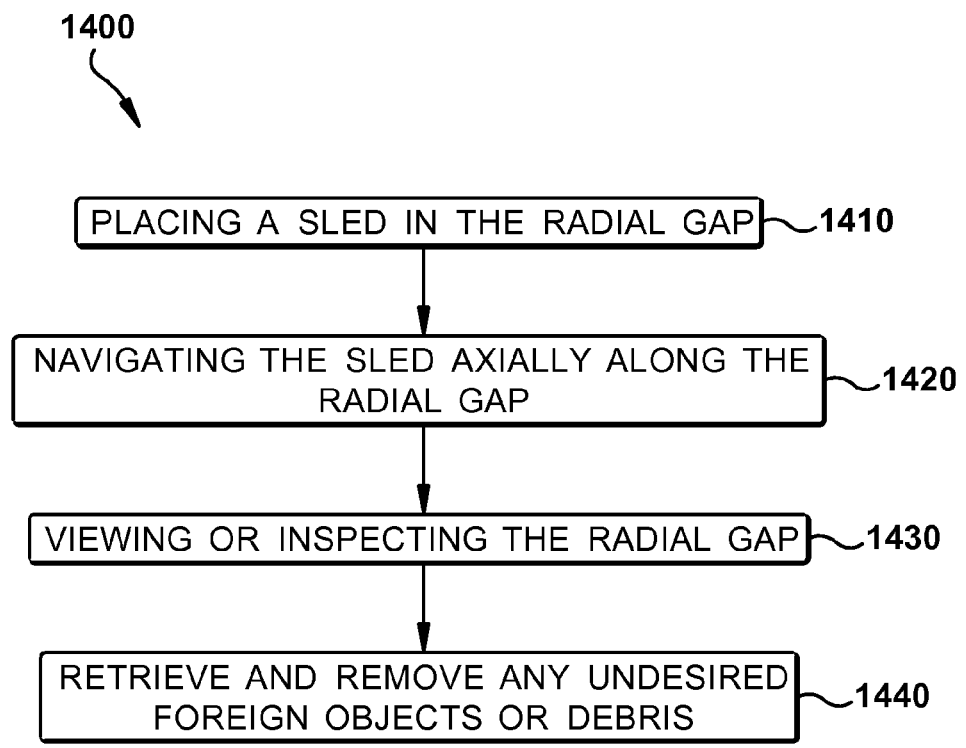
FIG. 14 illustrates a method for inspecting and/or servicing a dynamoelectric machine, according to an aspect of the present invention.

FIG. 14 illustrates a method for inspecting and/or servicing a dynamoelectric machine, according to an aspect of the present invention. The method 1400 includes the step 1410 of placing a sled in the radial gap 16 of the dynamoelectric machine (e.g., a motor or generator). The placing step 1410 may include installing an elongated guide member 1260 between the stator 12 and rotor 14 and securing at least one end of the elongated guide member by inflating a bladder 1370 that wedges itself between the rotor and stator. The other end of the elongated guide member may be tied off to any suitable support structure, or a second bladder may be used. In this example the elongated guide member 1260 is passed through a port 1202 on the second sled 1200. The placing step also includes installing an optical device 320, 1220 and/or a retrieval device 350, 1250 through one or more ports 340, 1240 in the first sled 300 or second sled 1200. A push rod 310, 1210 is also attached to a push rod attachment point 330, 1230.

A navigating step 1420 includes moving the first sled 300 or second sled 1200 axially along the radial gap by pushing or pulling on a push rod 310, 1210. A viewing or inspecting step 1430 is used to inspect the radial gap 16 for any undesired foreign objects or debris. The image output from the optical device may be transmitted to and viewed on any suitable computer or display. The optical device may be connected to the computer or display by any suitable conventional means (e.g., wired or wireless link). The viewing step 1430 may also include extending or retracting the optical device to view various portions of the radial gap. For example, 180 degrees of the radial gap can be viewed be extending the optical device so it travels circumferentially along the radial gap at various axial positions.

A retrieval step 1440 is used to retrieve and remove any undesired foreign objects or debris. The retrieval device 350, 1250 may comprise a clamp, a magnet, a snare, a gripper a fork and tine, a basket or a cutting tool. Some non-limiting examples of retrieval devices are illustrated in FIGS. 4-10. For example, a piece of broken wedge may be viewed by the optical device, grasped by the retrieval device and removed from the machine by retracting the push rod. This may all be accomplished by accessing a single end of the machine, thereby avoiding the need to disassemble both ends of the machine.

FIG. 15 is a perspective view of a sled, according to an aspect of the present invention. The sled 1500 includes a middle section 1504, and two end sections 1506. Each end section 1506 is connected to the middle section 1504 by a flexible member 1508. The middle section 1504, end sections 1506 and flexible member 1508 may be comprised of non-magnetic materials such as plastic, rubber, or non-magnetic metals or alloys. For example the flexible members 1508 may be formed of polypropylene or thinner portions of plastic, or corrugated plastic members. The flexible members 1508 permit the end sections 1506 to curve with the radially inner curved surface of the stator. Magnets 1509 are located in each of the end sections 1506, and the magnets 1509 may be flush with, proud of or recessed with respect to the surface of the end section. A removable guide block 1510 may be attached to one or both end sections 1506, and the guide block 1510 is used to ride along the stator slot 20 to help guide the sled 1500 as it travels axially along the radial gap 16. The sled 1500 includes an attachment point 1530 for the push rod 310. The attachment point may be an internally threaded hole configured for use with external threads on the end of push rod 310. One or more ports 1540 are configured for operation with the optical device 320 or the retrieval device 350.

FIG. 16 is a perspective view of a sled, according to an aspect of the present invention. The sled 1600 includes a middle section 1604, and two end sections 1606. The end sections and middle section may have rounded or tapered corners to facilitate travel along the radial gap. Each end section 1606 is connected to the middle section 1604 by a flexible member 1608. The flexible members 1608 may be formed of polypropylene or thinner portions of plastic, or corrugated plastic members, or any other suitable material. Magnetic guides 1610 are located on at least one of the end sections 1606, and the guides 1610 is used to ride along the stator slot 20 to help guide the sled 1600 as it travels axially along the radial gap 16. The sled 1600 includes an attachment point 1630 for the push rod 310. One or more ports 1640 are configured for operation with the optical device 320 and/or the retrieval device 350.

Figure 17:
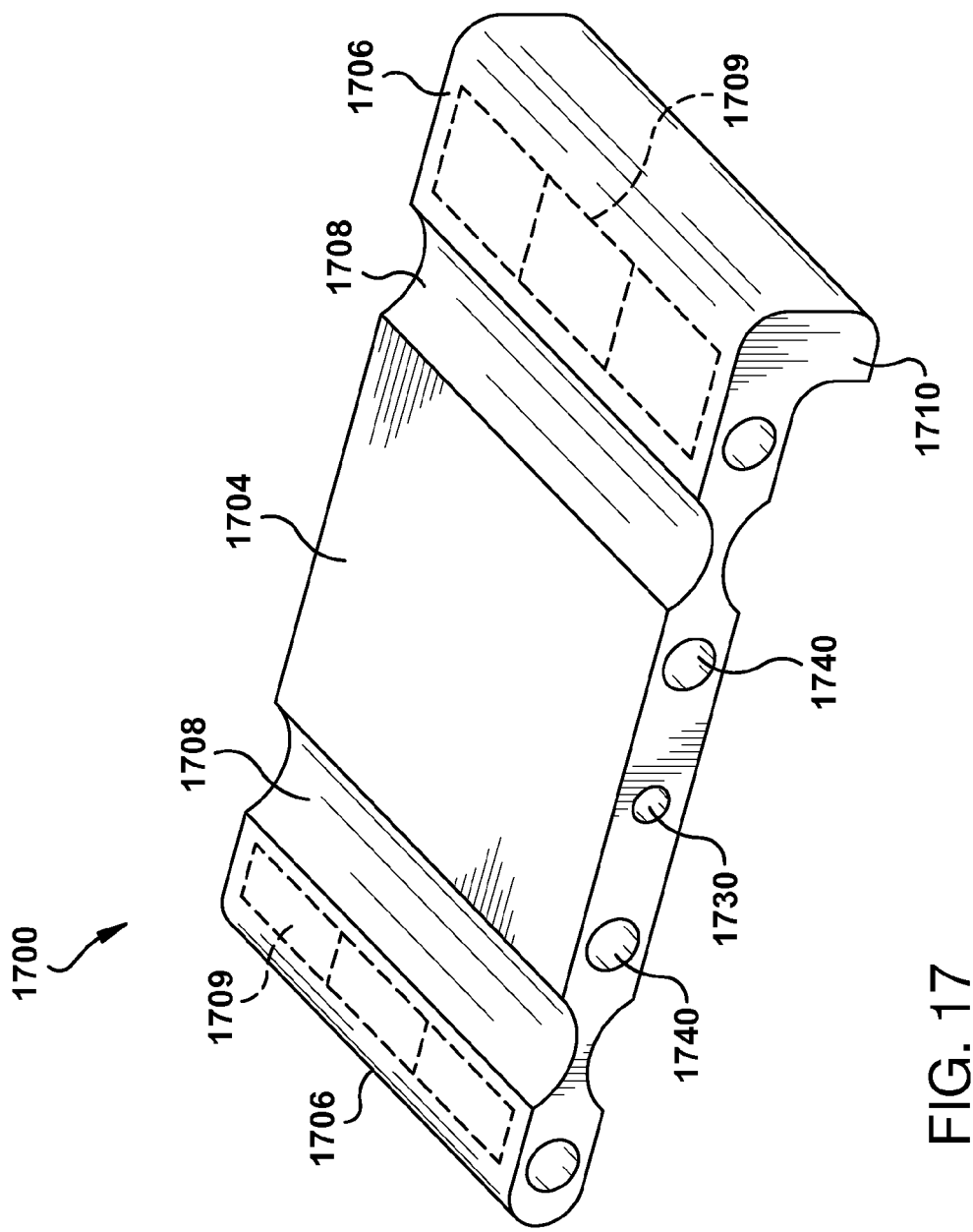
FIG. 17 is a perspective view of a sled, according to an aspect of the present invention.

FIG. 17 is a perspective view of a sled, according to an aspect of the present invention. The sled 1700 includes a middle section 1704, and two end sections 1706. Each end section 1706 is connected to the middle section 1704 by a flexible member 1708. The middle section 1704 and end sections 1704 may be formed of any suitable non-magnetic material, such as plastic or polypropylene. The flexible members 1708 are formed of the same or similar material, but with a thinner profile to permit flexibility. Magnets 1709 may be embedded within the end sections 1706. The built in guide 1710 is used to ride along the stator slot 20 to help guide the sled 1700 as it travels axially along the radial gap 16. The sled 1700 includes an attachment point 1730 for the push rod 310. One or more ports 1740 are configured for operation with the optical device 320 and/or the retrieval device 350.

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Further, while wedge assembly 29 has been illustrated as a stator wedge assembly, it is understood that other embodiments, such as a rotor wedge assembly, may be inspected without departing from the scope of the invention. Therefore, it is intended that the invention not be limited to the particular embodiment disclosed as the best mode contemplated for carrying out this invention, but that the invention will include all embodiments falling within the scope of the appended claims.

The invention claimed is:

1. A system for inspecting a dynamoelectric machine, the dynamoelectric machine comprising a rotor, a stator and a radial gap existing between the rotor and the stator, the system comprising:

a sled configured for insertion into the radial gap between the rotor and the stator, the sled configured to transport an optical device along the radial gap, the optical device configured to obtain an image of the radial gap, a portion of the rotor and a portion of the stator, the sled configured for attachment to a push rod and the push rod is used to move the sled and optical device along the radial gap, the sled comprising a main body having a middle section and two end sections, each end section connected to the main body by a flexible member;

an elongated guide member configured to cooperate with transportation of the sled, an expandable bladder located at one end of the elongated guide member, the elongated guide member including a conduit configured to supply a gas to the bladder for inflation and deflation of the bladder, the bladder configured to inflate and wedge itself between the rotor and the stator, wherein the sled has an aperture, the elongated guide member is configured to pass through the aperture so that the sled travels back and forth along the elongated guide member; and wherein, the system is configured for entry into a single end of the dynamoelectric machine.

2. The system of claim 1, the sled further comprising at least one magnet located in each of the end sections.

3. The system of claim 2, wherein the at least one magnet is located below a surface of the end section.

4. The system of claim 2, the sled further comprising:
an attachment point for the push rod; and
one or more ports configured for operation with the optical device or a retrieval device, a first port configured for operation with the optical device and a second port configured for operation with the retrieval device, the one or more ports passing through the middle section, the one or more ports configured to permit the optical device and the retrieval device to slide through the one or more ports.

5. The system of claim 4, wherein the optical device is a borescope and the retrieval device is at least one of:
a clamp, a magnet, a snare, a gripper, a fork and tine, a basket, or a cutting tool.

6. The system of claim 1, the sled further comprising:
an attachment point for the push rod; and
one or more ports configured for operation with the optical device or a retrieval device, a first port configured for operation with the optical device and a second port configured for operation with the retrieval device, the one or more ports configured to permit the optical device and the retrieval device to slide through the one or more ports.

7. The system of claim 6, wherein the optical device is a borescope and the retrieval device is at least one of:
a clamp, a magnet, a snare, a gripper, a fork and tine, a basket, or a cutting tool.

8. The system of claim 6, wherein at least one of the one or more ports is configured to turn at an angle, the angle being 30 degrees to 90 degrees.

9. The system of claim 1, the elongated guide member further comprising:
a hollow webbing material, a central portion of the hollow webbing material forming the conduit used to inflate and deflate the bladder.

10. A system for inspecting a dynamoelectric machine, the dynamoelectric machine comprising a rotor, a stator and a radial gap existing between the rotor and the stator, the system comprising:
a first sled configured for insertion into the radial gap between the rotor and the stator, the first sled configured to transport an optical device along the radial gap, the optical device configured to obtain an image of the radial gap, a portion of the rotor and a portion of the stator, the first sled configured for attachment to a push rod and the push rod is used to move the first sled and optical device along the radial gap;

a second sled having an aperture, an elongated guide member configured to cooperate with transportation of the second sled, an expandable bladder located at one end of the elongated guide member, wherein the elongated guide member includes a conduit configured to supply a gas to the bladder for inflation and deflation of the bladder, the bladder configured to inflate and wedge itself between the rotor and the stator, the elongated guide member is configured to pass through the aperture so that the second sled travels back and forth along the elongated guide member; and wherein, the system is configured for entry into a single end of the dynamoelectric machine.

11. The system of claim 10, the first sled further comprising a main body having a middle section and two end sections, each end section is connected to the main body by a flexible member, and at least one magnet located in each of the end sections.

12. The system of claim 11, wherein the at least one magnet is located below a surface of the end section.

13. The system of claim 10, both the first sled and the second sled further comprising:
an attachment point for the push rod; and
one or more ports configured for operation with the optical device or a retrieval device, a first port configured for operation with the optical device and a second port configured for operation with the retrieval device, the one or more ports passing through the middle section, the one or more ports configured to permit the optical device and the retrieval device to slide through the one or more ports.

14. The system of claim 13, wherein the optical device is a borescope and the retrieval device is at least one of:
a clamp, a magnet, a snare, a gripper, a fork and tine, a basket, or a cutting tool.

15. The system of claim 13, wherein at least one of the one or more ports of the second sled is configured to turn at an angle, the angle being 30 degrees to 90 degrees.

16. The system of claim 10, the elongated guide member further comprising:
a hollow webbing material, a central portion of the hollow webbing material forming the conduit used to inflate and deflate the bladder.

17. A method for inspecting or servicing a dynamoelectric machine, the method comprising the steps of:
installing an elongated guide member between a stator and a rotor of the dynamoelectric machine, and securing at least one end of the elongated guide member by inflating a bladder, the bladder configured to wedge itself between the rotor and stator once inflated,
placing a sled over the elongated guide member;
installing at least one of an optical device and a retrieval device through one or more ports in the sled;
placing the sled in a radial gap between the rotor and the stator, the sled configured for insertion into the radial gap, the sled configured to transport the optical device along the radial gap, the optical device configured to obtain an image of the radial gap, the sled configured for attachment to a push rod and the push rod is used to move the sled and the optical device along the radial gap, the sled comprising a main body having a middle section and two end sections, each end section connected to the main body by a flexible member;
navigating the sled axially along the radial gap by pushing or pulling on the push rod;

inspecting the radial gap by viewing an image produced from the optical device to identify presence of any foreign object or debris; and retrieving and removing any foreign object or debris identified in the inspecting step.

\* \* \* \* \*